(12) United States Patent
Wilson et al.

(10) Patent No.: US 6,361,528 B1
(45) Date of Patent: Mar. 26, 2002

(54) DYNAMICALLY COMPLIANT CATHETER

(75) Inventors: Robert F. Wilson, Roseville; Douglas J. Duchon, Chanhassen, both of MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 09/286,142

(22) Filed: Apr. 5, 1999

(51) Int. Cl.[7] ............................................. A61M 31/00
(52) U.S. Cl. ...................... 604/500; 600/435; 604/158
(58) Field of Search ................. 604/104, 264, 604/523, 158, 500, 506–509; 600/433–435

(56) References Cited

U.S. PATENT DOCUMENTS

| 3,570,485 A | 3/1971 | Reilly |
| 4,401,433 A | 8/1983 | Luther |
| 4,406,656 A | 9/1983 | Hattler et al. |
| 4,498,902 A | 2/1985 | Ash et al. |
| 4,540,404 A | 9/1985 | Wolvek |
| 4,563,180 A | 1/1986 | Jervis et al. |
| 4,601,713 A | 7/1986 | Fuqua |
| 4,710,181 A | 12/1987 | Fuqua |
| 4,738,666 A | 4/1988 | Fuqua |
| 4,846,791 A | * 7/1989 | Hattler et al. |
| 4,950,232 A | 8/1990 | Ruzicka et al. |
| 5,102,401 A | 4/1992 | Lambert et al. |
| 5,106,368 A | 4/1992 | Uldall et al. |
| 5,176,659 A | 1/1993 | Mancini |
| 5,256,150 A | 10/1993 | Quiachon et al. |
| 5,282,781 A | 2/1994 | Liprie |
| 5,389,091 A | 2/1995 | Moorehead |
| 5,472,418 A | 12/1995 | Palestrant |
| 5,474,537 A | 12/1995 | Solar |
| 5,484,418 A | 1/1996 | Quiachon et al. |
| 5,498,239 A | 3/1996 | Galel et al. |
| 5,533,968 A | 7/1996 | Muni et al. |
| 5,573,508 A | * 11/1996 | Thornton ..................... 604/96 |
| 5,618,267 A | 4/1997 | Palestrant |
| 5,653,697 A | 8/1997 | Quiachon et al. |
| 5,707,354 A | 1/1998 | Salmon et al. |
| 5,735,831 A | * 4/1998 | Johnson et al. ............. 604/280 |

FOREIGN PATENT DOCUMENTS

| FR | 1.211.941 A | 3/1960 |
| JP | 404002362 A | 1/1992 |

* cited by examiner

*Primary Examiner*—Mark Bockelman
(74) *Attorney, Agent, or Firm*—James W. Inskeep; Oppenheimer Wolff & Donnelly LLP

(57) ABSTRACT

A catheter enabling a reduced puncture hole size into the skin and blood vessel is disclosed. In one embodiment, the catheter has an elongate body having an expandable sheath extending at least a portion of its length. A pressure constraining sheath is positioned to surround the expandable sheath, at a selected region to prevent expansion of the inner sheath at the region of the constraining sheath. In one preferred use, the constraining sheath is positioned at the puncture hole. During use, the catheter increases in cross-section by an expandable sheath expanding from a first diameter to a second diameter. However, the outer sheath does not expand, maintaining a small diameter at the puncture site.

13 Claims, 3 Drawing Sheets

DYNAMICALLY COMPLIANT CATHETER

FIELD OF THE INVENTION

This invention relates generally to angiography and/or particularly to an improved catheter for injecting medical fluids such as radiographic contrast fluid into living organisms.

BACKGROUND OF THE INVENTION

Angiography is a procedure used in the treatment of cardiovascular conditions including abnormalities or restrictions in blood vessels of a human or animal body. During angiography, a radiographic contrast material is injected through a catheter into a vein or artery, which then passes to vascular structures in fluid communication with the vein or artery. When X-rays are passed through the region of the body into which the contrast material is injected, they are absorbed by the contrast material, providing radiographic images of the desired vascular structure(s). The images can be recorded on film or video tape and/or displayed on a fluoroscope monitor. The images can be used for many purposes, as for example diagnostics, and for operative procedures such as angioplasty, wherein a balloon is inserted into a vascular system and inflated to open a stenosis.

The contrast material can be injected into the catheter by either manual or automated injection systems. Although the apparatus for injecting the contrast material can vary, many current systems include a syringe operatively connected with the catheter. The syringe has a chamber for holding the contrast material and a plunger reciprocally moveable within the chamber. An example of one such apparatus is U.S. Pat. No. 5,573,515, the entire disclosure of which is incorporated herein by reference. In this apparatus, the contrast material is suctioned into the chamber when the plunger is moved to create a partial vacuum within the chamber. A reversal of the plunger direction first forces air out of the chamber and then delivers the contrast material to the catheter at a rate and volume determined by the speed of movement of the plunger.

In a manual system the user or operator loads the syringe and ejects air from the chamber before connecting the syringe to the catheter. The user of a manual system adjusts the rate and volume of injection by altering the manual force applied to the plunger. The maximum injection pressure for manual systems is typically limited to 200 p.s.i. (i.e. the maximum pressure that can be applied by the human hand), and the maximum quantity of fluid is about 12 cc.

Angiography can include the injection of fluids other than the contrast material. For example, a saline flush and/or the injection of fluid medications may be desired.

The catheter through which the contrast agent or other fluid is supplied is typically inserted percutaneously and into the desired artery or vein. When inserted percutaneously, a puncture hole is created in both the skin and blood vessel wall at the insertion point in order to correctly position the catheter. It is preferable to use a puncture hole that is as small as possible, to avoid leakage around the catheter and to minimize the subsequent wound size. Additionally, the larger the puncture hole, the greater the opportunity for complications and the more time needed to stop the bleeding after the catheter is removed.

Many presently available catheters have a fixed size (diameter) that extends the entire length of the catheter. Resistance to fluid flow in the catheter is determined by the inside diameter. Therefore, the size of catheter chosen for a specific procedure is based upon the inside diameter needed to achieve the particular flow rates associated with the procedure. However, such fixed diameter catheters have the same outside diameter at the puncture site as at other points on the catheter. As a result of this design, the wound at the puncture site may be unduly large for the particular procedure to be performed.

Although the presently available catheters are well accepted by the medical profession and function as required, it is desirable to have a catheter that minimizes the vascular puncture site diameter, but allows minimal resistance to fluid flow. In other words, it is desirable to provide a catheter that minimizes the trauma to a patient but provides versatility to the user for many varied applications and uses of the catheter.

OBJECTS OF SUMMARY OF THE INVENTION

In view of the foregoing, it is an object of the present invention to overcome the deficiencies of existing catheters.

It is a further object of the present invention to provide a catheter that minimizes the wound size for use of the catheter and yet still provides a wide variety of potential uses.

It is a further object of the present invention to provide a catheter that is economical to produce.

It is a further object of the present invention to provide a method of ensuring adequate fluid flow through a catheter with the smallest diameter patient incision as possible.

The present invention attempts to address these objects and other objects not specifically enumerated herein through the use of a catheter that has an outer surface, a portion of which is compliant and has an adjustable diameter and another portion which is not adjustable, or non-compliant. It further may include a backbone, a compliant and expandable sheath surrounding the backbone, and an outer non-compliant sheath which covers a portion of the expandable sheath. At least a portion of the outer non-compliant sheath is not expandable.

The backbone allows the catheter to retain a predetermined shape for ease of manipulation and placement of the catheter. The outer non-compliant, nonexpandable sheath limits the expansion of the catheter and is positioned at the insertion point into the patient. The adjustable sheath, however, expands. Thus, the catheter retains the narrow insertion point but expands at either side of the insertion point.

The catheter sheath selectively expands to provide an expanded area and a non-expanded area, which expansion may occur either during, or prior to, the injection of a fluid. This selective expansion is advantageous because the puncture hole at the entry site into the patient is minimized.

In a preferred method of inserting the catheter, the flexible catheter tip and body are compressed, folded or otherwise manipulated to be smaller in diameter than the diameter of outer non-compliant sheath. The outer sheath can be inserted through the skin and vascular wall after which the body of the catheter is inserted through the constraining outer sheath. The body is then expanded to the desired size.

In a second embodiment, there may be no discrete inner expandable sheath at the position where the outer non-compliant sheath is located. Instead, the nonexpandable sheath may be integral with the expandable sheath.

In a further embodiment, the backbone can be removable and replaceable with a different backbone in order to provide a different shape to the catheter.

In yet a further embodiment, the outer non-compliant sheath may be expandable on demand, for example by mechanical structures. This option may be desired when a large device, such as an atherectomy catheter, needs to be inserted through the catheter. Alternately, the outer sheath may be replaceable with an outer sheath having a larger diameter.

DETAILED DESCRIPTION

Figure 1:
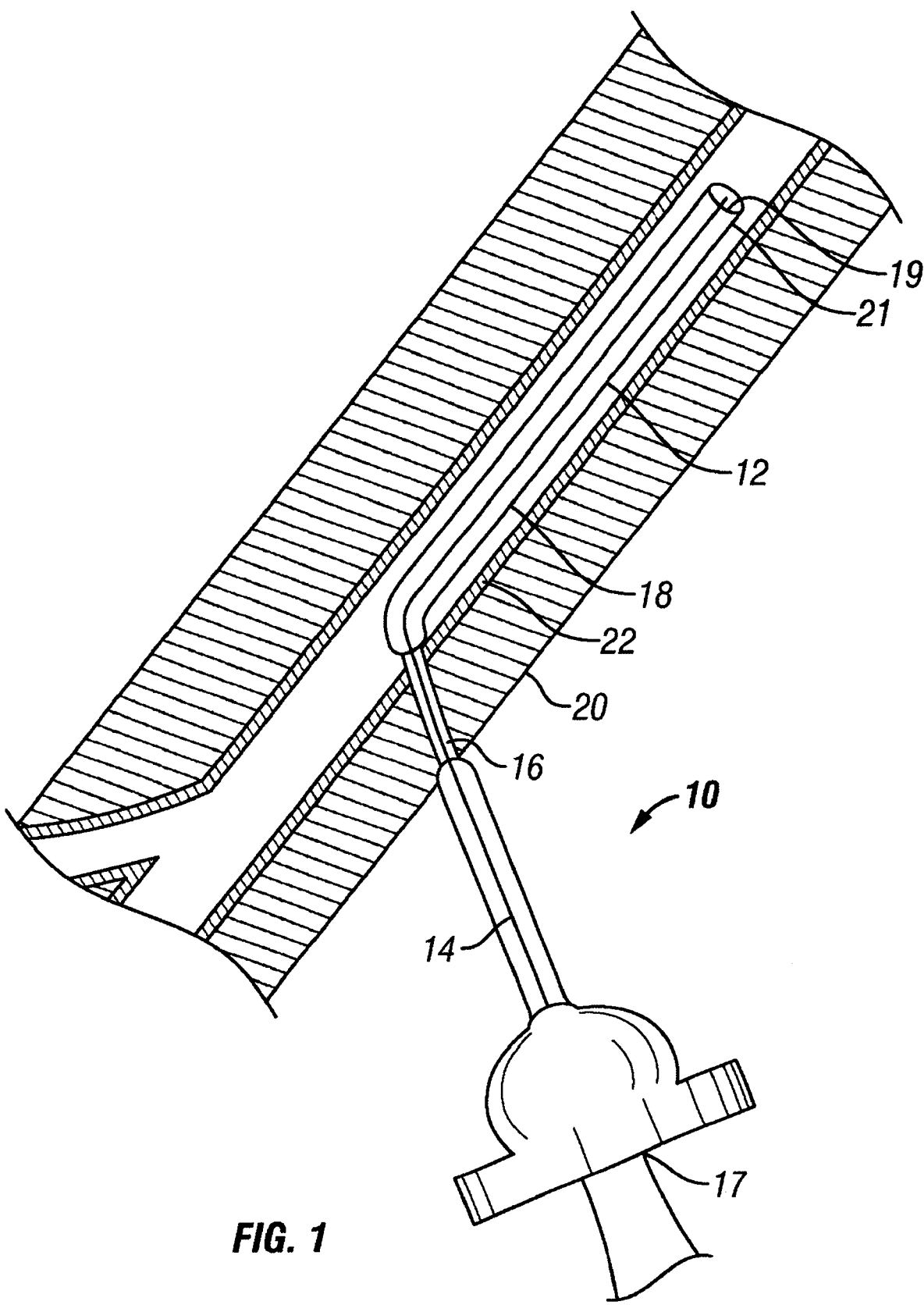
FIG. 1 is a cross-sectional view of a catheter of the invention inserted into a blood vessel of a patient.

Referring to FIG. 1, a catheter 10 in one embodiment of the present invention is shown inserted into a patient to supply fluids, for example a contrast agent, to the blood stream. The catheter 10 is inserted into the patient through a puncture hole in the patient's skin 20 and in a blood vessel wall 22.

Figure 2:
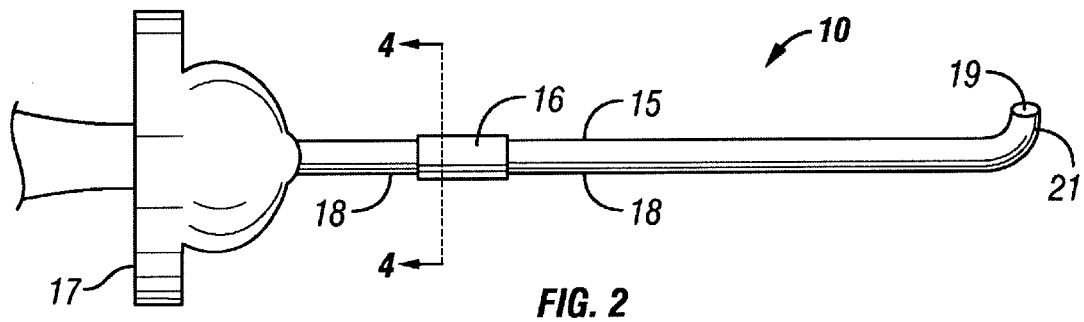
FIG. 2 is a perspective side view of a catheter of the invention in an unexpanded, first position.
Figure 3:
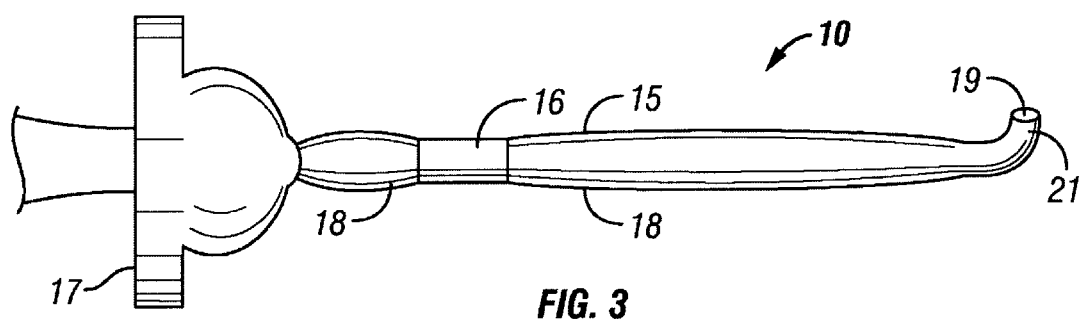
FIG. 3 is a perspective side view of the catheter of FIG. 2 in an expanded, second position.

Referring to FIGS. 1, 2 and 3, the catheter 10 has a hollow elongate body 12 that extends from the patient's exterior and terminates inside the blood vessel. The distal end 21 of the catheter 10 is the end inserted into the patient whereas the proximal end of the catheter 10 is the end closest to the user (usually a physician or clinician).

Located internally in the catheter 10 is a backbone 14, which serves to shape the catheter 10. The backbone 14 is shown as an interior structure of the catheter 10 and is encompassed by the conduit 15 of the catheter 10, which conduit is the outermost portion of the catheter 10. The backbone 14 further provides strength, structure and integrity to the catheter 10 to allow insertion of the catheter 10 into the patient. The backbone 14 is generally sufficiently rigid to penetrate the patient's skin and vessel wall into the lumen of the vessel. However, the backbone 14 is also fairly thin so that unnecessary bulk and thickness are not added to the catheter 10.

The conduit 15 of the catheter 10 includes an outer sheath 16 and an inner sheath 18 wherein the outer sheath 16 is a noncompliant, non-expandable sheath and wherein the inner sheath 18 is a compliant, expandable sheath that can readily stretch or expand or both, for example by the pressure of fluid flowing therethrough.

The interior of the conduit 15 is a hollow passage and is designed to provide a passage for fluid or a medical device, for example contrast agent or angioplasty catheter, respectively, or any other applicable liquid or device. In the case of fluid, the fluid enters the catheter 10 at an inlet 17 located at the proximal end of the catheter 10, passes through the interior of the conduit 15, and exits the catheter 10 at an outlet 19 at the distal end 21 of the catheter 10. The inlet 17 can include typical connector systems such as Luer® locks, threads, and other known systems. The pressure of the fluid passing through the catheter 10 may be sufficient to expand expandable sheath 18, but is insufficient to expand outer sheath 16.

The outer sheath 16 is located at the point on the catheter 10 where the catheter 10 passes through the skin and vascular wall. The outer sheath 16 is rigid, non-compliant and non-expandable, and should be able to withstand pressures of at least about 500 p.s.i., preferably at least about 750 p.s.i., and more preferably at least about 1200 p.s.i. without radially expanding or deforming. The diameter of the outer sheath 16 is directly related to the diameter of the puncture hole needed for insertion of the catheter 10 into the patient. It is preferable to have the outer sheath 16 as small as possible so as to minimize the puncture hole. Preferably, the outer diameter of the outer sheath 16 is about 0.8 to 5 mm.

An inner expandable sheath 18 extends the length of the catheter's elongate body 12 and surrounds and covers the backbone 14. If the backbone 14 is in the interior of catheter 10, the inner sheath 18 is preferably connected to the backbone 14 in several spots, for example, at the tip 19. Alternatively, the backbone 14 may be integral with the inner sheath 18, that is, the backbone 14 may be located within the wall of the inner sheath 18.

FIG. 2 shows catheter 10 of the present invention in a first, or non-expanded position prior to insertion in a patient. The inner sheath 18 has a diameter less than or equal to the outer sheath 16. Preferably, the tip 19 of the catheter (at distal end 21) and the inner sheath 18 have a diameter less than the outer sheath 16.

FIG. 3 shows the catheter 10 in a second, or expanded position. In this position, the inner sheath 18 has expanded to a diameter greater than that of the outer sheath 16. The inner sheath 18 has expanded from its first position in FIG. 2 to a second position in FIG. 3. The outer sheath 16 has not expanded or distorted, but has retained the same diameter and shape as before the inner sheath 18 was expanded.

Having described the general structure of a first embodiment of the present invention, the various components and variants thereof are now discussed in greater detail. It will be understood that a catheter in accordance with the present invention may incorporate any number of combinations of the specific aspects of the disclosed components.

Backbone

The backbone 14 of the catheter 10 extends longitudinally along the body and provides the catheter 10 with much of its structural properties. Additionally, the backbone 14 will allow the catheter 10 to be advanced to the preferred location in the blood vessel or may allow for rotation of the catheter 10 once in position.

The backbone 14 of the catheter 10 may be similar to the backbones used in conventional catheters. Moreover, the backbone 14 is typically about 60 to 100 cm long and generally extends the length of the catheter 10.

Figure 4:
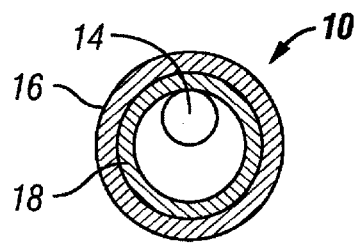
FIG. 4 is a cross-sectional view of a catheter of the invention taken along line 4—4 of FIG. 2.
Figure 5:
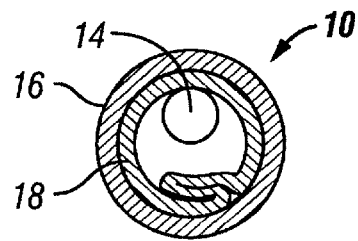
FIG. 5 is a cross-section view of another embodiment of the invention taken along line 4—4 of FIG. 2.
Figure 6A:
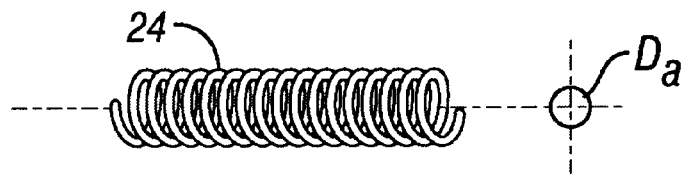
FIG. 6A is a perspective side view of a spring in expanded form.
Figure 6B:
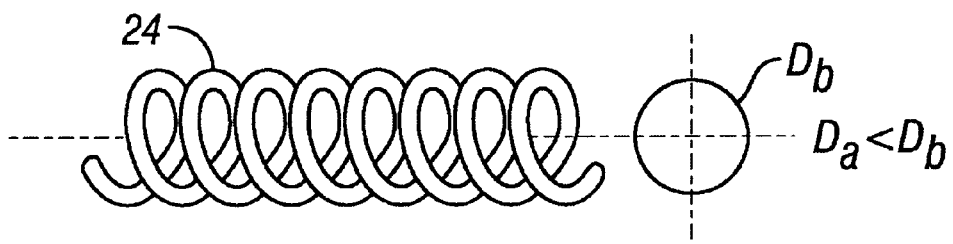
FIG. 6B is a perspective side view of a spring in unexpanded form.
Figure 7A:
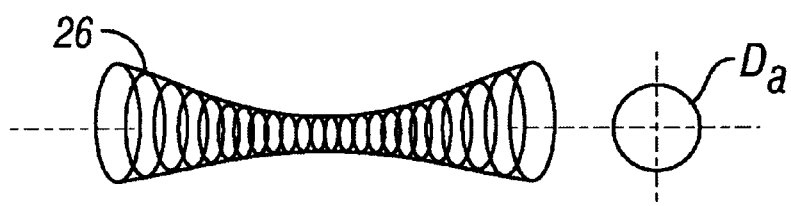
FIG. 7A is a perspective side view of a coil in expanded form.
Figure 7B:
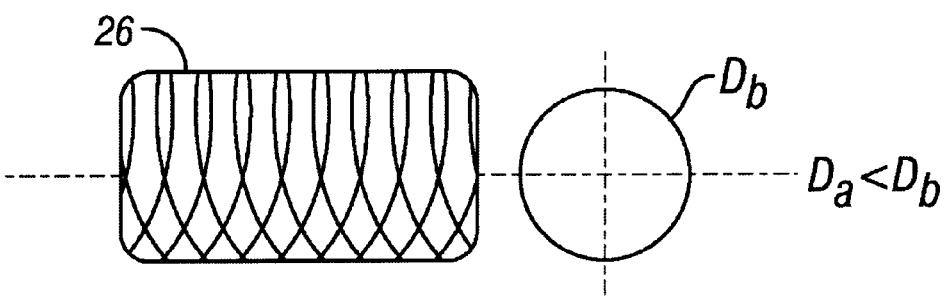
FIG. 7B is a perspective side view of a coil in unexpanded form.

The backbone 14 is generally located within the conduit 15 of the catheter 10. That is, it is embedded in the catheter 10, either in the interior of the conduit 15 or within a wall of the conduit 15; that is, the backbone 14 is positioned transmurally. Alternatively, the backbone 14 may be centrally located in the hollow interior of the conduit 15 or it may be displaced to one side or another of the interior. FIGS. 4 and 5 show the backbone 14 placed to one side of the interior area of conduit 15.

Another alternative embodiment is to provide the backbone 14 within a lumen of the catheter 10; that is, the backbone 14 is positioned intralumenally. If positioned in a lumen, the backbone 14 is typically loosely held so that the backbone 14 can be rotated and advanced as desired. The lumen may be positioned inside or outside of the inner and outer sheaths 16, 18. Generally, when a backbone 14 is said to be "removable" and/or "replaceable", the backbone 14 is positioned in a lumen, however backbones 14 located in the interior of the catheter 10 may also be removable and replaceable.

Examples of typical backbone 14 materials include thermoplastic and thermoset polymers, such as nylon, polypropylene, polyethylene, polycarbonate, metals and alloys, such as titanium, stainless steel, ceramics, and composite materials, which can include combinations of ceramics, organic polymers, inorganic materials, and metals. A preferred material is a Ni—Ti shape-memory alloy commonly known as "nitinol".

In one embodiment, the backbone 14 is removable from the catheter 10 after insertion in a patient and replaceable with a different backbone 14, one that, for example, changes the shape of the catheter 10. When exchanging the backbone 14, it is not necessary to replace or move the catheter 10. In particular, it is not necessary to disturb the puncture hole where the outer sheath 18 is positioned.

Outer Sheath

At least a portion of the outer sheath 16 is a rigid, noncompliant, non-expandable section. This non-compliant outer sheath 16 maintains a minimal puncture hole in the skin and vascular wall through which the catheter 10 is passed. Preferably, the puncture hole is less than about 3 mm.

The outer sheath 16 constrains the inner sheath 18 such that the inner sheath 18 is constrained from expanding beyond a predetermined limit established by the outer sheath 16. The outer sheath 16 is positioned at least at the site of entry of the catheter 10 into the body and the vessel. The outer sheath 16 maintains the diameter of the catheter 10 minimally small at the puncture hole, yet allows expansion of the catheter 10 (in particular the compliant sheath 18) along its length either on both the distal and proximal sides of the outer sheath 16 or on one side of the outer sheath 16. The unexpanded area created by the outer sheath 16 restricts the flow of the contrast agent through the catheter 10 yet allows sufficient volume flow of the agent.

The outer sheath 16 may be permanently affixed to the inner expandable sheath 18 it may be movable along the length of the catheter 10. For example, when a movable outer sheath 16 is used, the user is capable of positioning the outer sheath 16 in the desired position on the catheter 10. This may be particularly useful in patients where it is not possible to get a deep penetration of the catheter 10 into and along the blood vessel. Additionally, a movable outer sheath 16 may be completely removed from the catheter 10 and replaced with a different diameter outer sheath 16.

In some embodiments it may be desirable to provide an outer sheath 16 that is expandable at some location or locations along its length. For example, the outer sheath 16 may be designed to remain at its unexpanded diameter at the outer sheath 16 mid-point and then expand gradually each direction along its length. This configuration may increase the stability of the catheter at the puncture point.

Controlled expansion of portions of the outer sheath 16 or of the entire outer sheath 16 itself may be accomplished by material selection, or by mechanical means. For example, once the catheter 10 is correctly positioned, the portion of the outer sheath 16 immediately on each side of the puncture point may be expanded, for example by a "twist and lock" or other mechanism. Any expansion of the outer sheath 16 may be directly controllable by the user, or may be a function of the fluid pressure flowing through the catheter 10. The expandable portions may have a single expanded position or may be incrementally expandable. However, at least some portion of the outer sheath 16 usually remains unexpanded from its initial diameter.

The outer sheath 16 is preferably a cylindrical tube, but other shapes may be utilized if desired. The length of the outer sheath 16 is typically about 5 to 30 cm. Generally, the outer sheath 16 will be positioned so that it is located at the skin 20 and vessel puncture hole and extends minimally in either direction past this point. Preferably, the non-compliant, non-expanding outer sheath 16 extends at least 5 mm past the puncture point in the skin 20 and blood vessel wall 22.

The diameter of the outer sheath 16 should be as small as feasible to provide as small of a puncture hole as possible insofar as the diameter of the outer sheath 16 is directly related to the diameter of the puncture hole needed for insertion of the catheter 10 into the patient. The outer sheath 16 should not, however, be so small as to prevent insertion of the compliant sheath 18 and catheter backbone 14 therethrough.

Typically, the outer sheath 16 will have an outer diameter between about 1 and 4 mm, preferably 1 to 2 mm. Different sizes of the outer sheath 16 can be available for different uses. The inner wall diameter should be minimally less than the outer diameter. That is, it is preferable to have the wall of the outer sheath 16 as thin as possible without compromising strength and integrity. Typical wall thickness include 0.004 to 0.010 mm, but other thickness may be utilized depending on the specific outer sheath 16 material used.

The outer sheath 16 is preferably manufactured from medically acceptable materials such as metals (for example stainless steel or nitinol), plastics (for example nylon, urethane or Polyethylene Terephthalate (ET)), and composites. The material of the outer sheath 16 may be reinforced, for example by fibers or other strengthening agents, so as to further increase the tensile strength and decrease any distortion possibilities. The outer sheath 16 should be capable of constraining pressure in excess 500 p.s.i., preferably more than 750 p.s.i. more preferably more than 1200 p.s.i. (approximately 8 atmospheres) in the radial direction without expanding or distorting in shape or size. In another preferred embodiment, the outer sheath 16 is capable of resisting pressures between about 1200–1500 p.s.i. without distorting. Many materials can have their properties, such as elasticity and stiffliess, etc., altered by various processing methods.

Inner Expandable Sheath

Placed within the outer non-compliant sheath 16 is an inner expandable sheath 18 that generally extends the length of the catheter 10. In embodiments where the backbone 14 is located in the interior of the catheter 10, the inner sheath 18 surrounds the backbone 14. It is through the inner sheath 18 that the fluid being administered, for example the contrast fluid, passes. The expandable sheath 18 is radially expandable, preferably by the pressure of the fluid flowing therethrough, preferably in a controlled and repeatable manner. The amount of expansion, or diameter change, can be designed to be responsive to the needs of the user.

The expandable sheath 18 can be radially adjusted from a first diameter to a second diameter with the use of fluid pressure, mechanical means, or other forces. The first diameter of the inner sheath 18 is generally less than the smallest diameter of the outer sheath 16, whereas the second diameter of the inner sheath 18 is greater than the largest diameter of the outer sheath 16. The expansion of the inner sheath 18 to the second diameter may either be a permanent or temporary deformation, that is, it may be capable of returning to the first diameter without any permanent deformation. Any expansion may be incremental.

The expandable sheath 18 can be manufactured from medically acceptable materials such as metals, plastics, and composites, however polymeric materials are preferred. Insofar as the expandable sheath 18 must be capable of expanding from one diameter to at least a second diameter, it is preferable that the material used for the expandable sheath is elastic. However, expandability may be achieved by other methods, such as by providing an inner sheath 18 that has sufficient non-elastic material to provide a circumference related to the second diameter. The inner sheath 18 is then folded upon itself inside the outer sheath 16.

FIGS. 4 and 5 show cross-sectional views of two embodiments of the inner sheath 18 placed within the outer sheath 16. FIGS. 4 and 5 are taken from line 4—4 in FIG. 2. FIG. 4 shows the inner sheath 18 flatly and continuously disposed within the outer sheath 16. In such an embodiment, the inner sheath 18 is elastic and will expand radially at the points where the outer sheath 16 is not present when pressure is applied from the inside.

The inner sheath 18 of FIG. 5 will likewise expand radially at the points where the outer sheath 16 is not present, however, the inner sheath 18 is not elastic or is likely less elastic than that disclosed in FIG. 4. Rather, extra material of the inner sheath 18 is folded on itself so that when pressure is applied, the inner sheath 18 will unfold, thus providing an expanded diameter.

Methods of Expanding the Expandable Sheath

The expandable sheath 18 may be expanded by mechanical means, fluid pressure, or other feasible methods. In a first embodiment, the expandable sheath 18 expands simply as a result of an increase in fluid pressure passing through the catheter 10. The initial pressure of the fluid causes the inner sheath 18 to expand at locations where it is not constricted by the outer sheath 16. The catheter 10 remains in this expanded configuration for the duration of the procedure after which the catheter 10 collapses or is simply pulled out through the narrower outer sheath 16.

In another embodiment, mechanical means, such as a spring 24 or coil 26, as shown in FIGS. 6A, 6B, 7A and 7B, can be used to expand the inner sheath 18. For example, a tightly wound spring 24 may be part of the catheter 10 between the backbone 14 and the expandable sheath 18. The spring 24 may be actuated by mechanical manipulation, such as a twisting or pulling, in order to increase the diameter of the catheter 10.

In yet another embodiment, the backbone 14 of the catheter 10 may also be used as a "key" or other device to alter the catheter's 10 shape. The backbone 14 may be removed and inserted in a manner that distorts the expandable sheath 18 so that a second diameter is obtained. Alternately, a stylet (other than the backbone 14) can be placed inside the catheter 10 for manipulation of the catheter's 10 shape and size.

And in another embodiment, the expandable inner sheath 18 may be made from a material that is expandable when heated, such as nitinol. Application of heat to the catheter 10 may cause the inner sheath 18 to expand whereas removal of the heat, or cooling, will cause the inner sheath 18 to retract to, or close to, its original diameter. Alternatively, the patient's body temperature (typically 98.60° F.) may be sufficient to cause the inner sheath 18 to expand.

The foregoing description addresses embodiments encompassing the principles of the present invention. The embodiments may be changed, modified and/or implemented using various types of arrangements. Those skilled in the art will readily recognize various modifications and changes which may be made to the invention without strictly following the exemplary embodiments and applications illustrated and described herein, and without departing from the scope of the invention which is set forth in the following claims.

I claim:

1. A method of introducing fluids through a wound and into tissue by radially expanding a catheter that includes an inner sheath and a movable outer sheath comprising:

positioning the outer sheath along an area of the wound;

introducing a fluid having an initial pressure within a conduit created by the inner sheath;

increasing the pressure of the fluid to cause expansion of at least a portion of the inner sheath;

constricting the expansion of the inner sheath with said outer sheath at least at a site of the wound; and maintaining the constriction provided by the outer sheath so as to limit expansion forces encountered by said wound as a result of expansion of said inner sheath.

2. The method of claim 1, wherein the initial pressure of the fluid causes the inner sheath to expand at locations where it is not constricted by the outer sheath.

3. The method of claim 1 wherein the catheter remains in an expanded configuration for a duration of a procedure.

4. The method of claim 1 further comprising:

ensuring adequate fluid flow through the catheter with a smallest diameter patient wound size.

5. The method of claim 1 further comprising:

incrementally increasing the expand on of the inner sheath.

6. The method of claim 1 further comprising:

removing the inner sheath by pulling the inner sheath out through the outer sheath.

7. The method of claim 1 further comprising:

removing the inner sheath by collapsing the inner sheath.

8. A method of radially expanding a catheter comprising:

providing a catheter having a non-expandable outer sheath and an expandable inner sheath;

inserting said catheter into a puncture hole in a patient;

positioning said non-expandable outer sheath at said puncture hole;

applying expanding means to said catheter for expanding said inner sheath;

constricting an expansion of the inner sheath with said outer sheath at least at a site of the puncture hole: and maintaining the constriction provided by the outer sheath so as to limit expansion forces encountered by said puncture hole as a result of expansion of said inner sheath.

9. The method of claim 8 wherein said expanding means is a fluid.

10. The method of claim 8 further comprising:

ensuring adequate fluid flow through the catheter with a smallest diameter puncture hole size.

11. The method of claim 8 further comprising:

incrementally increasing the expansion of the inner sheath.

12. The method of claim 8 further comprising:

removing the Inner sheath by pulling the inner sheath out through the outer sheath.

13. The method of claim 8 further comprising:

removing the inner sheath by collapsing the inner sheath.

* * * * *